US012788570B2

(12) United States Patent
Kirwan

(10) Patent No.: US 12,788,570 B2
(45) Date of Patent: Nov. 10, 2026

(54) FEMORAL PROSTHETIC COMPONENT

(71) Applicant: David Kirwan, Wirlinga (AU)

(72) Inventor: David Kirwan, Wirlinga (AU)

( * ) Notice: Subject to any disclaimer, the term of this patent is extended or adjusted under 35 U.S.C. 154(b) by 248 days.

(21) Appl. No.: 18/863,160

(22) PCT Filed: May 19, 2023

(86) PCT No.: PCT/AU2023/050424
§ 371 (c)(1),
(2) Date: Nov. 5, 2024

(87) PCT Pub. No.: WO2023/220784
PCT Pub. Date: Nov. 23, 2023

(65) Prior Publication Data
US 2025/0302633 A1 Oct. 2, 2025

(30) Foreign Application Priority Data
May 20, 2022 (AU) ................................ 2022901351

(51) Int. Cl.
*A61F 2/36* (2006.01)
*A61F 2/30* (2006.01)

(52) U.S. Cl.
CPC .......... *A61F 2/3609* (2013.01); *A61F 2/3607* (2013.01); *A61F 2002/30125* (2013.01); *A61F 2002/365* (2013.01)

(58) Field of Classification Search
CPC ........................................................ A61F 36/09
See application file for complete search history.

(56) References Cited

U.S. PATENT DOCUMENTS

2002/0128720 A1 9/2002 Masini
2013/0096690 A1 4/2013 McCoy

FOREIGN PATENT DOCUMENTS

FR 2645012 A1 10/1990
WO 2019015962 A1 1/2019

OTHER PUBLICATIONS

International Search Report & Written Opinion dated Jun. 28, 2023 from PCT Application No. PCT/AU2023/050424, 10 pages.

*Primary Examiner* — Andrew Yang
(74) *Attorney, Agent, or Firm* — INNOVATION CAPITAL LAW GROUP, LLP; Vic Lin

(57) ABSTRACT

A femoral prosthetic component has a stem and a neck. The neck defines a centre of rotation when engaging a head articulating within an acetabular cup in use. The component has anterior offset so that the centre of rotation is anteriorly offset with respect to a longitudinal axis of the stem. A proximal portion of the neck has posterior angulation. This three-dimensional geometry, including in the longitudinal plane, increases range of motion and mitigates against impingement.

32 Claims, 7 Drawing Sheets

FEMORAL PROSTHETIC COMPONENT

FIELD OF THE INVENTION

This invention relates generally to total hip arthroplasty. More particularly, this invention relates to a type of femoral prosthetic component.

BACKGROUND OF THE INVENTION

A femoral prosthetic component has a stem which is inserted into the femoral canal during total hip replacement, and which defines a neck to engage a head articulating within a corresponding acetabular cup component.

The femoral component may be implanted cemented or cementless and may be sized according to anatomical considerations. In addition, the femoral component is usually sized according to lateral and vertical offset in the frontal plane which provide a resultant offset between the native femur and the pelvis.

These lateral and vertical offsets are usually ascertained from an A-P radiograph and are chosen to accommodate, maintain and restore patient specific bone geometry and, to allow for adequate range of motion, stability and minimum bone impingement.

These femoral stem components are usually left and right-handed interchangeable (i.e. non side-specific and, symmetric with respect to the frontal plane), thereby allowing for reduced inventory.

The present invention seeks to provide a femoral prosthetic component which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE DISCLOSURE

There is provided herein a femoral prosthetic component which has three-dimensional geometry including in the longitudinal plane to increase range of motion and mitigate against impingement.

The present femoral prosthetic component comprises a stem and a neck. The neck defines a centre of rotation when engaging a head articulating within an acetabular cup in use.

The component has anterior offset so that the centre of rotation is anteriorly offset with respect to a longitudinal axis defined by the stem. The anterior offset increases anterior range of motion until anterior bone impingement, typically caused by the sulcus of the femur impinging the anterior inferior iliac spine of the pelvis (AIIS) in full flexion. In this scenario, the anterior offset positions the sulcus of the femur further away from the AIIS in full flexion, thereby increasing the anterior range of motion until bone impingement occurs, unless remote impingement such as knee on chest action occurs, or unless posterior soft tissue restraints prevent further movement. Such anterior offset may however increase the likelihood of posterior implant impingement, wherein the neck impinges against the posterior rim of the acetabular cup.

As such, a proximal portion of the neck has posterior angulation. The posterior angulation increases posterior range of motion until posterior implant impingement. The proximal and distal portions of the neck described herein are described with reference to the insertion orientation of the component wherein the general convention is therefore to describe the proximal portion of the neck as being towards the patient's head and the distal portion of the neck towards the patient's feet.

The anterior offset may be defined by anterior translation and/or angulation of the neck with respect to the stem.

For example, the anterior angulation may be between 5° and 20°, and approximately 15° in an embodiment. Furthermore, the posterior angulation may be between 10° and 30°, approximately 23°. The net effect of the anterior offset and posterior angulation may result in the centre of rotation being anteriorly offset from a frontal plane coincident with the longitudinal axis of the stem by between 3 and 10 mm, approximately 6 mm in an embodiment.

The component may be designed according to the sizing of the acetabular cup so that a posterior angulation transition point generally coincides with the rim of the acetabular cup component, thereby maximising the posterior range of motion.

At least one portion along the neck may have a cross-section having a flattened or diminutive postero-superior aspect. For example, the cross-section may define an ellipse having a major axis and a minor axis, and the major axis may define a rotational angle with respect to the longitudinal axis of the stem in the longitudinal plane. The rotational angle may be more than 10°, even approximately 30° in embodiments.

The diminutive postero-superior aspect increases the posterior range of motion in full hip flexion where anterior boney impingement usually occurs before anterior prosthetic impingement and thus prevents anterior prosthetic impingement. In other words, should anterior prosthetic impingement be possible or even occur, the diminutive postero-superior aspect increases range of motion into flexion by increasing the distance between the rim of the acetabular cup and the side of the neck. The diminutive postero-superior aspect also reduces point impingement by presenting a flatter side of the neck to the rim of the cup, thereby reducing likelihood of mechanical failure of the rim of acetabular component, or of the neck. Impingement induced instability is also thereby reduced or avoided.

In embodiments, the rotational angle may increase (i.e. rifling) from a distal end of the neck towards a proximal end of the neck. The neck may be configured so that the rotational angle increases to a maximum rotational angle at a location of the neck generally coincident with the rim of the cup.

Rifling of the axes of the ellipse of the neck is beneficial in relation to posterior impingement in extension and anterior impingement in flexion.

Furthermore, the major axis of the ellipse is beneficially orientated to withstand ground reaction force heel strike loading which varies but is maximal at about 30° of hip flexion when walking.

According to one aspect, there is provided a femoral prosthetic component comprising a stem and a neck, the neck defining a centre of rotation when engaging a head articulating within an acetabular cup in use, wherein the component has anterior offset so that the centre of rotation may be anteriorly offset with respect to a longitudinal axis of the stem and a distal portion of the neck has posterior angulation.

A distal portion of the neck may form a trunnion which engages a socket of the head.

The anterior offset may be defined above a juncture between the neck and the stem (i.e. above the osteotomyline), thereby avoiding modification of the stem itself and therefore standardised instrumentation and orthopaedic procedure The component may be configured so that the juncture generally coincides with an osteotomy plane when implanted in use.

The anterior offset may be defined by anterior translation between the neck and the stem. The anterior translation may be more than 2 mm.

The anterior offset may be defined by anterior angulation between the neck in the stem.

The anterior angulation may be defined between a longitudinal axis of a proximal portion of the neck and a frontal plane coincident with a longitudinal axis of the stem. In an osteotomy plane, the anterior angulation may be between 3° and 25°. In an osteotomy plane, the anterior angulation may be approximately 15°.

The posterior angulation may be defined between a longitudinal axis of the distal portion of the neck and a longitudinal axis of a proximal portion of the neck. The posterior angulation may be between 10° and 30°. The posterior angulation may be approximately 23°.

The centre of rotation may be anteriorly offset from a frontal plane coincident with the longitudinal axis of the stem by between 3 and 10 mm. The centre of rotation may be anteriorly offset from a frontal plane coincident with the longitudinal axis of the stem by approximately 6 mm.

An angle defined by a longitudinal axis of a distal end of the neck and a frontal plane defined by the longitudinal axis of the stem may be between 5 and 20°. An angle defined by a longitudinal axis of a distal end of the neck and a frontal plane defined by the longitudinal axis of the stem may be approximately 8°.

The neck may define a posterior angulation transition point between a distal portion and a proximal portion thereof. The transition point may generally coincide with a rim of the acetabular cup in use. The transition point may be more than halfway along the neck from a distal end of the neck. The transition point may be approximately two thirds along the neck from a distal end of the neck.

At least one portion along the neck may have a cross-section having a diminutive postero-superior aspect. The cross-section may define a major axis and a minor axis and the major axis may define a rotational angle with respect to the longitudinal axis of the stem in the longitudinal plane. The cross-section may be elliptical. The rotational angle may be more than 10°. The rotational angle may be more than 15°. The rotational angle may be approximately 30°.

The rotational angle may increase along the neck from a distal end of the neck. The rotational angle increases to a maximum rotational angle along the neck. The position of the maximum rotational angle may be generally coincident with a location of impingement of the neck against a rim of the cup in use.

The component may further comprise a further femoral component and the further femoral component may be symmetric with the femoral component in a longitudinal plane.

According to another aspect, there is provided total hip arthroplasty involving the femoral prosthetic component described herein, the arthroplasty comprising implanting the component between a native femur and pelvis so that a centre of rotation defined by the neck when engaging a head articulating within an acetabular cup may be anteriorly offset with respect to a longitudinal axis of the stem and a proximal portion of the neck may have posterior angulation.

According to another aspect, there is provided a femoral prosthetic component comprising a stem and a neck and wherein the neck has a cross-section having a diminutive postero-superior aspect.

The cross-section defines a major axis and a minor axis and wherein the major axis defines a rotational angle with respect to the longitudinal axis of the stem in the longitudinal plane.

The cross-section may be elliptical.

The rotational angle may be more than 10°. The rotational angle may be more than 15°. The rotational angle may be approximately 30°.

The rotational angle may increase along the neck from a distal end of the neck.

The rotational angle may increase to a maximum rotational angle along the neck. The position of the maximum rotational angle may be generally coincident with a location of impingement of the neck against a rim of the cup in use.

Other aspects of the invention are also disclosed.

BRIEF DESCRIPTION OF THE DRAWINGS

Notwithstanding any other forms which may fall within the scope of the present invention, preferred embodiments of the disclosure will now be described, by way of example only, with reference to the accompanying drawings in which.

DESCRIPTION OF EMBODIMENTS

Figure 1:
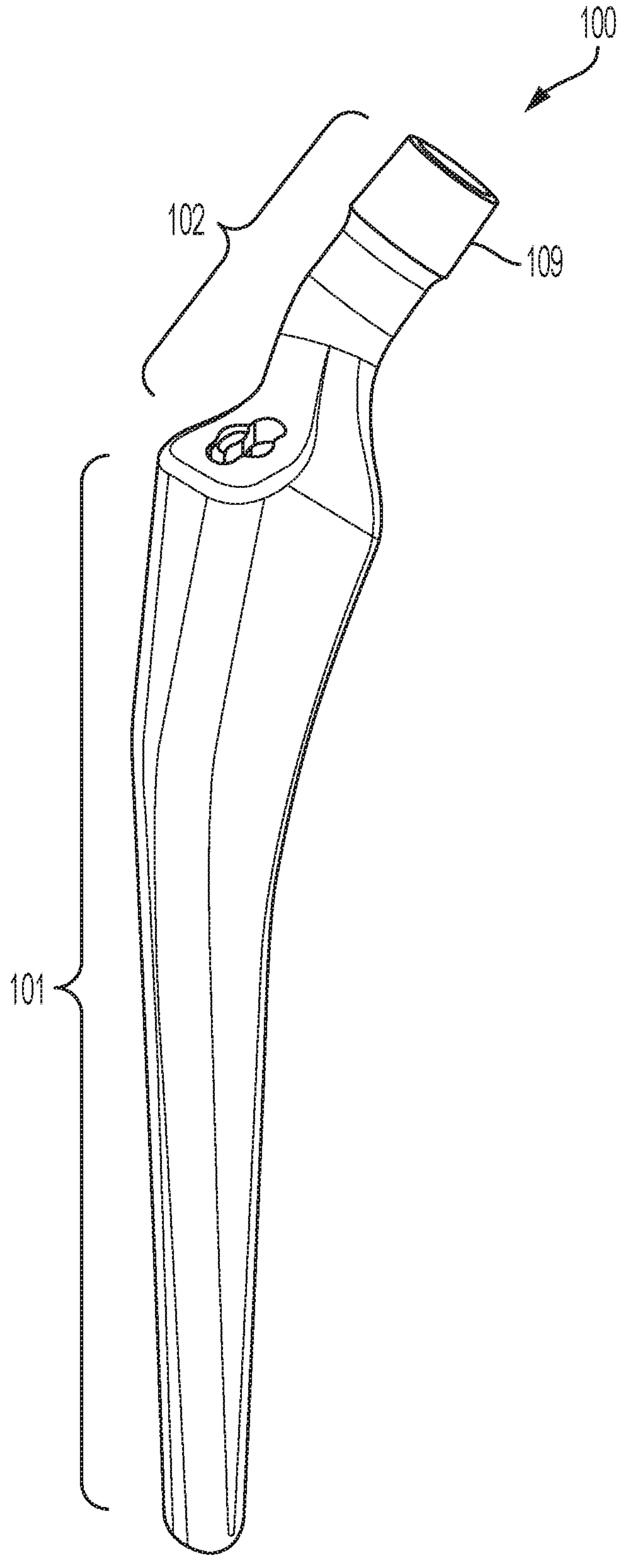
FIG. 1 shows a perspective view of a left femoral prosthetic component in accordance with an embodiment.

FIG. 1 shows a femoral prosthetic component 100 comprising a stem 101 and a neck 102.

Figure 17:
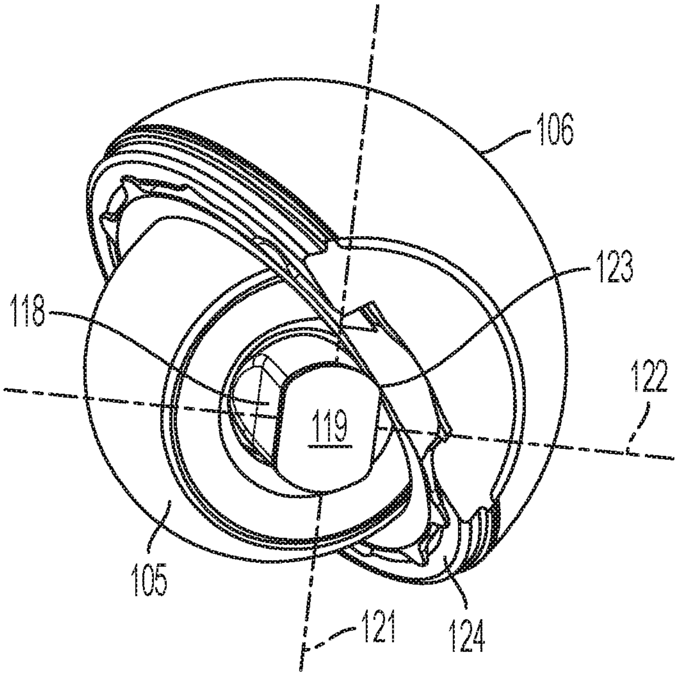
FIGS. 17 and 18 compare posterior impingement of a conventional femoral prosthetic component neck as compared to that of the present component.
Figure 18:
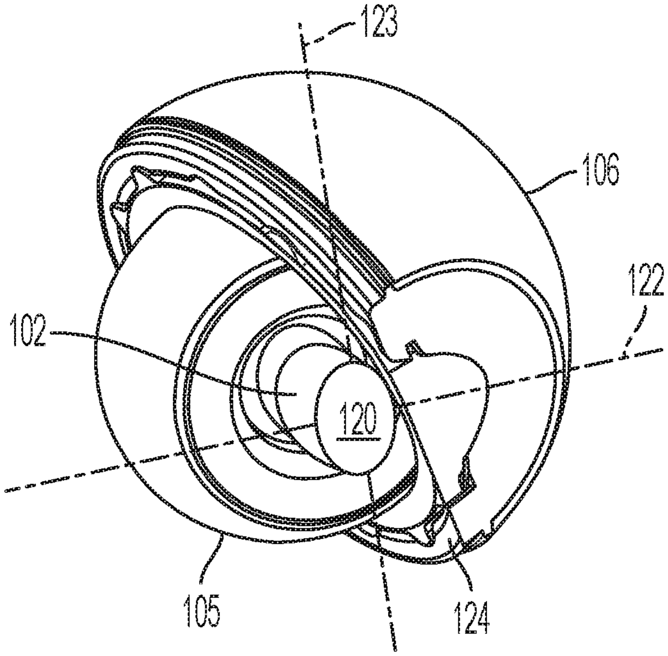

During total hip arthroplasty, the stem 101 is inserted cemented or cementless into the femoral canal with the neck 102 protruding therefrom to engage a head 105 articulating within an acetabular cup 106 in the manner shown in FIGS. 17 and 18.

Figure 13:
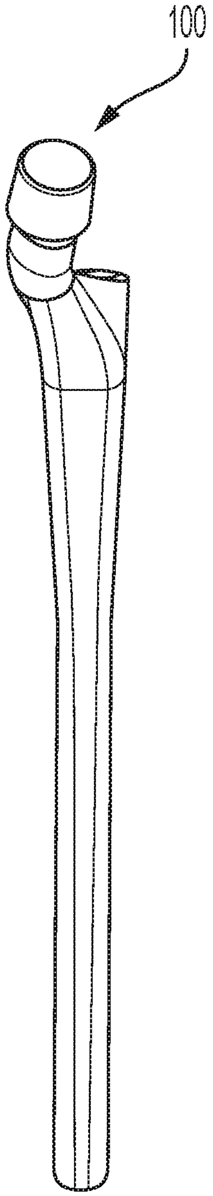
FIG. 13 shows a medial elevation view of a right-sided version of the component.

The component 100 is left or right-handed with the illustrations showing the left-side version of the component 100, except FIG. 13 which shows a symmetrical right-side version of the component 100.

Figure 2:
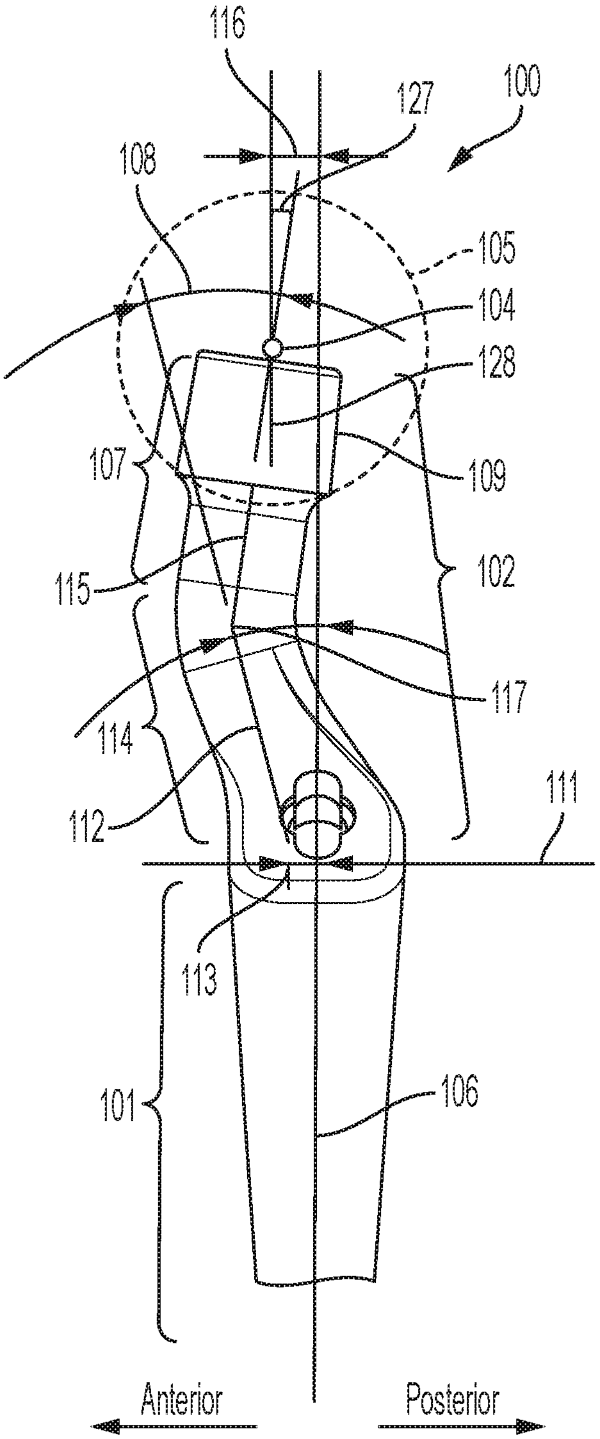
FIG. 2 shows exemplary geometry of the neck of the component.

FIG. 2 shows the neck 102 defining a centre of rotation 104 when engaging the head 105 articulating within an acetabular cup 106.

The component 100 has anterior offset so that the centre of rotation 104 is anteriorly offset (shown as 116 in FIG. 2) with respect to a longitudinal axis 129 defined by the stem 101.

The anterior offset increases anterior range of motion until anterior bone impingement. Anterior bone impingement may be caused by the sulcus of the femur impinging the anterior inferior iliac spine of the pelvis (AIIS) in full flexion. In this scenario, the anterior offset positions the sulcus of the femur further away from the AIIS in full flexion, thereby increasing the anterior range of motion until bone impingement may occur.

Furthermore, a proximal portion 107 of the neck 102 has posterior angulation 108 to increase posterior range of motion until posterior implant impingement may occur. The posterior angulation 108 counteracts the decreased posterior rotational range to implant impingement caused by the anterior offset.

The proximal portion 107 may form and include a trunnion 109 which engages a socket of the head 105.

In general terms, with reference to FIG. 2, posterior angulation 108 may be defined by the orientation of a longitudinal axis of a proximal portion 107 of the neck (usually defining the trunnion 109) with respect to a frontal plane defined by the longitudinal axis 129 of the stem 101.

Figure 3:
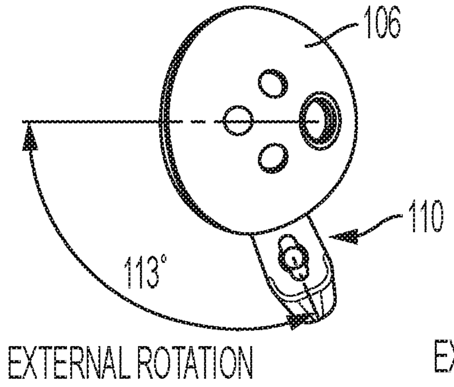
FIGS. 3-6 illustrate decreased posterior range of motion (in external rotation) involving a 40/20 cup in hyperextension with external rotation of a conventional femoral prosthetic component as compared to the present component.
Figure 4:
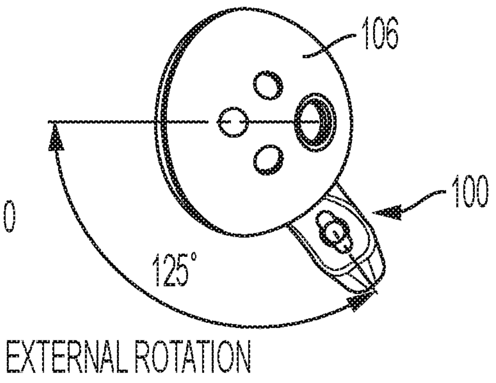
Figure 5:
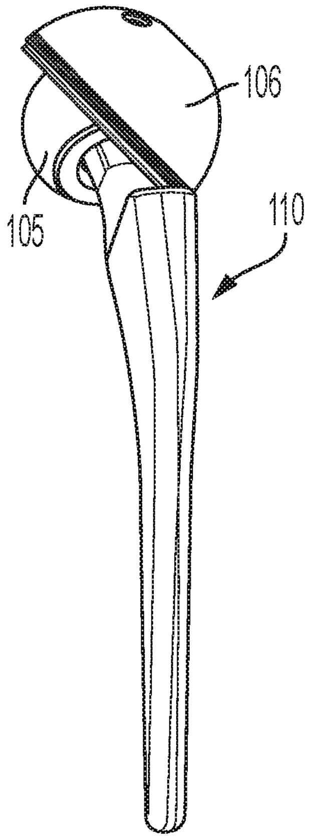
Figure 6:
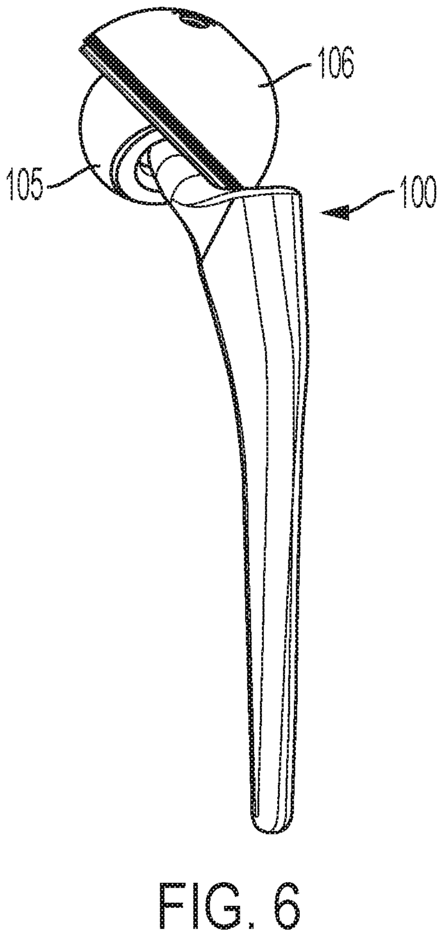
Figure 7:
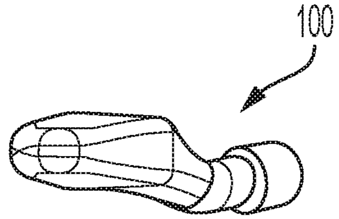
FIG. 7 shows a bottom plan view of the component.
Figure 8:
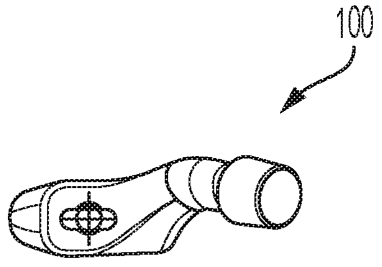
FIG. 8 shows a top plan view of the component.

FIGS. 3 and 5 compares scenarios involving a 40/20 cup in hyperextension showing exemplary external rotation of approximately 113° of a conventional stem 110 (which is symmetric with respect to the frontal plane) to approximately 125° of the present stem 101.

Figure 9:
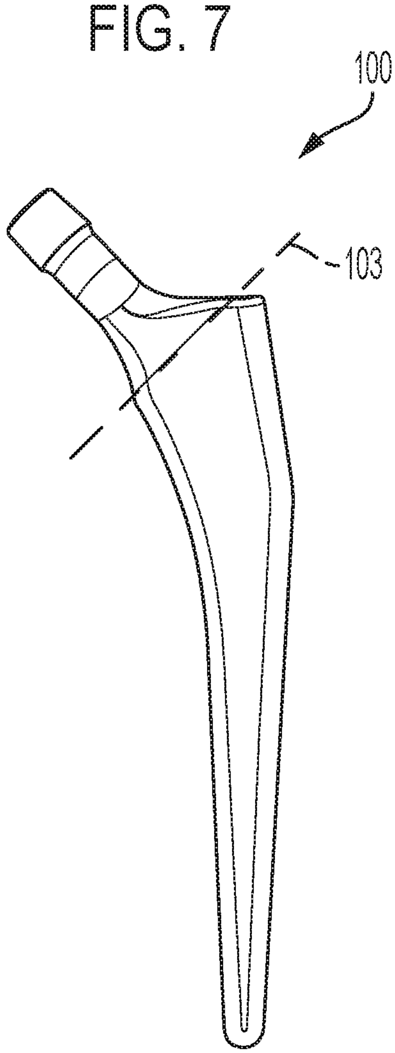
FIG. 9 shows an anterior elevation view of the component.
Figure 10:
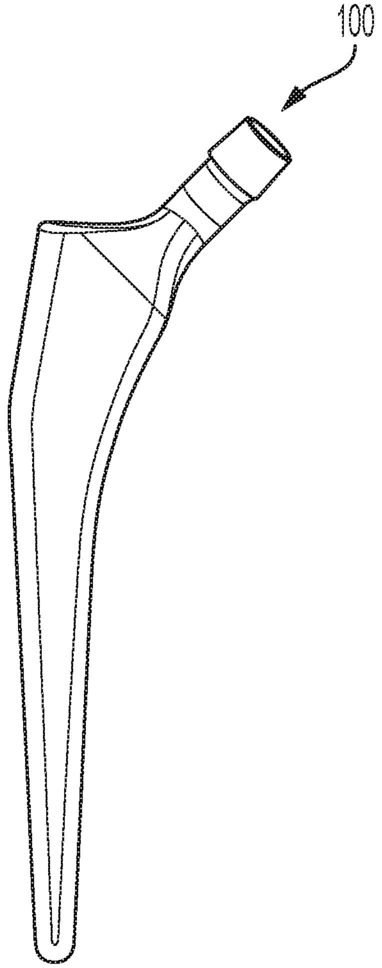
FIG. 10 shows a posterior elevation view of the component.
Figure 11:
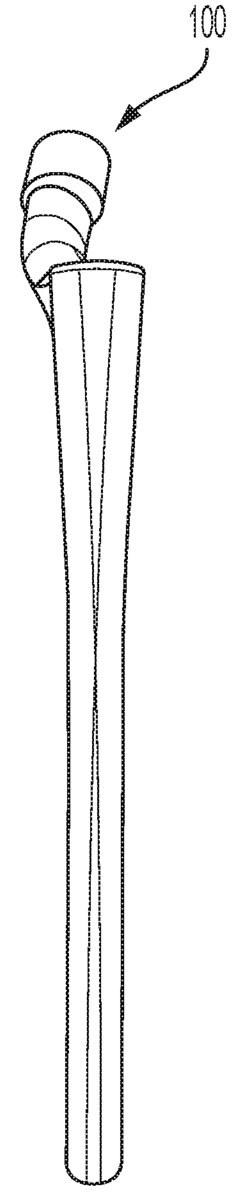
FIG. 11 shows a lateral elevation view of the component.
Figure 12:
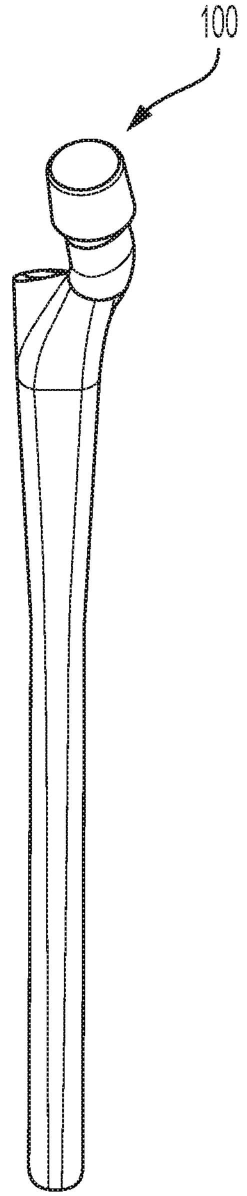
FIG. 12 shows a medial elevation view of the component.

FIG. 2 shows the component 100 generally along an osteotomy plane 103 shown in FIG. 9.

The anterior offset may be provided in a variety of ways, including anterior translation or angulation of a superior portion of the stem 101. Even where the stem 101 has anterior angulation, the stem 101 would yet define a predominant longitudinal axis 129.

However, in a preferred embodiment, the anterior offset is defined by the neck 102 above a juncture between the neck 102 and the stem 101. In other words, the anterior offset may be defined entirely above the osteotomy plane 103.

The anterior offset may be defined by the neck 102 having anterior translation 111 with respect to the stem 101 as is shown in FIG. 2. More specifically, a distal end 113 of a longitudinal axis 112 of a distal portion 114 of the neck 102 may be offset with respect to a frontal plane defined by the longitudinal axis 129.

In the embodiments shown in FIG. 2, the anterior translation 111 may be approximately 4 mm.

The anterior offset may be defined by the neck 102 having anterior angulation with respect to a frontal plane defined by the longitudinal axis 129 of the stem 101.

From this perspective, the distal portion 114 of the neck 102 may be anteriorly angled (such as at the level of the osteotomy) between 5° and 20° with respect to the frontal plane defined by the longitudinal axis 129 of the stem 101. In one embodiment, the distal portion 114 of the neck 102 is anteriorly angled at approximately 15° with respect to the frontal plane coincident with the longitudinal axis of the stem 101.

From the osteotomy plane perspective shown in FIG. 2, the posterior angulation 108 may be defined between the longitudinal axis 112 of the distal portion 114 of the neck 102 and a longitudinal axis 115 of the proximal portion 107 of the neck 102. From this perspective, the posterior angulation 108 may be between 1° and 30°, approximately 23° in an embodiment.

The net offset of the anterior offset and posterior angulation of the neck 102 may result in the centre of rotation 104 having anterior offset 116 from a frontal plane coincident with the longitudinal axis 129 of between 4 and 10 mm, approximately 6 mm in embodiments.

Furthermore, the net angulation 127 of the anterior angulation (as defined by the longitudinal axis 112 of the distal portion 114 of the neck 102) and the posterior angulation (as defined by the longitudinal axis 115 of the proximal portion 107 of the neck 102) may result in a net posterior angulation (i.e., that which is defined by the longitudinal axis 115 of the proximal portion 107 of the neck 102 and a frontal plane 128 defined by the longitudinal axis 129 of the stem 101) of between 5 and 20°, approximately 8° in embodiments.

The neck 102 may generally define a posterior angulation transition point 117 between the proximal portion 107 and the distal portion 114. The location of the transition point 117 preferably generally coincides with the position of the rim 124 of the acetabular cup 106. As such, the location of the transition point 117 may be defined according to the size of the acetabular cup 106.

The transition point 117 may be more than halfway along the neck 102 from a distal end of the neck 102. The transition point 117 may be approximately two thirds along the length of the neck 102 from the distal end of the neck 102.

As shown in FIG. 2, the neck 102 may form a smooth curve (i.e., curvature devoid of sharp side transitions) with respect to the transition point 117.

In embodiments, at least one portion along the neck 102 may have a cross section 120 having a diminutive postero-superior aspect to further increase the posterior range of motion in full hip flexion until postero-superior impingement against the rim 124 of the cup 106. In other words, should anterior prosthetic impingement be possible or even occur, the diminutive postero-superior aspect increases range of motion into flexion by increasing the distance between the rim 124 of the acetabular cup 106 and the side of the neck 102. The diminutive postero-superior aspect also to reduces point contact loading against the rim 124 of the cup 106 which could cause stress or fracture the neck 102, damage to the cup 106 or instability (dissociation between the femoral head 105 and cup 106.

Figure 14:
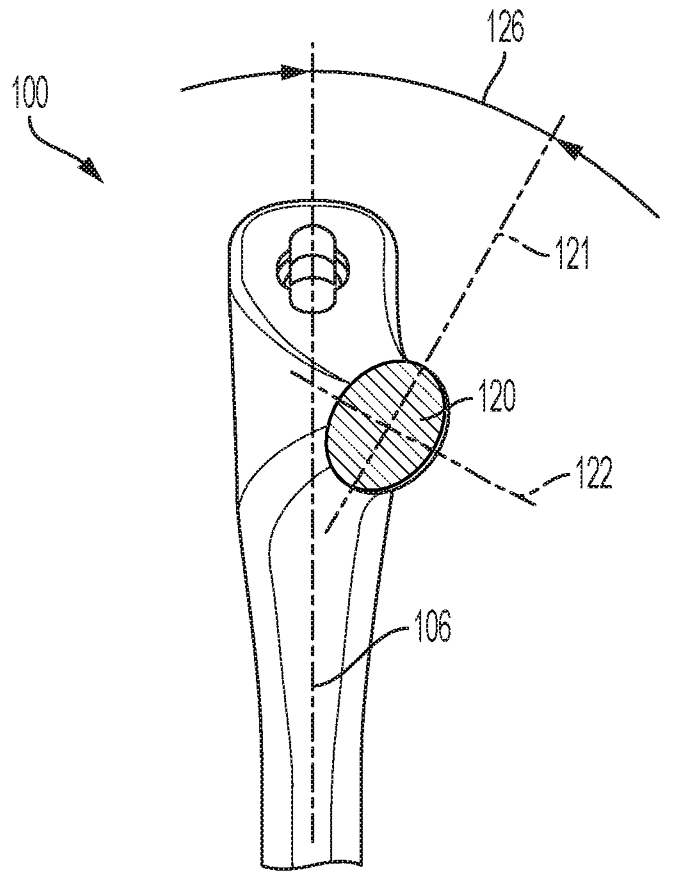
FIG. 14 shows a cross-section of the neck in accordance with an embodiment.

In the embodiment shown in FIG. 14, the cross section 120 defines a major width axis 121 and a minor width axis 122 and wherein the major axis 121 defines a rotational angle 126 with respect to the longitudinal axis 129 of the stem 101. The rotational angle 126 is preferably more than 10°. In the embodiment shown, the rotational angle 126 is approximately 30°.

FIG. 17 illustrates a typical cross-section 119 of a conventional neck 118 wherein the major axis 121 is usually aligned along the longitudinal axis 129 of the stem 101 to increase the strength thereof when standing vertically. As can be appreciated from FIGS. 17, the cross-section 119 has relatively sharp edges 123 which exacerbate point loading against the rim 124 of the acetabular cup 106 in the event of posterior implant impingement. As alluded to above, this point loading may stress or fracture the neck 118 or damage the cup 106.

However, FIG. 18 shows the effect of the major axis angulation of the present neck 102 which not only increases the posterior rotational range to cup impingement but also presents a flatter side of the neck 102 against the rim 124 of the acetabular cup 106, thereby reducing point loading stresses on the neck 102 as well as impingement induced instability.

In the preferred embodiment shown, the cross section 120 is elliptical.

Figure 15:
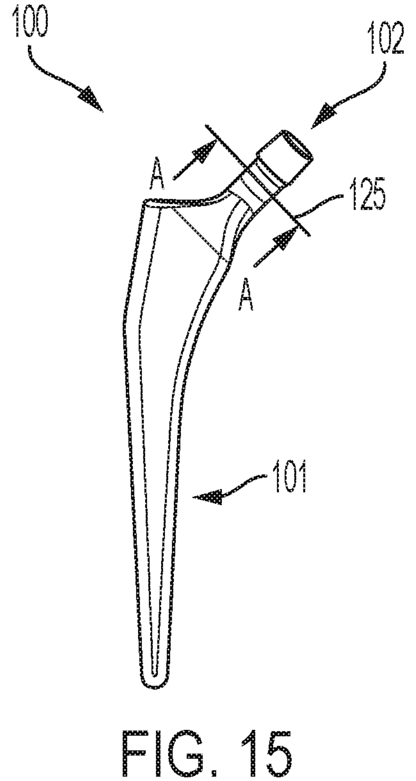
FIGS. 15 and 16 show a further cross-section of the neck at an impingement location of the neck.
Figure 16:
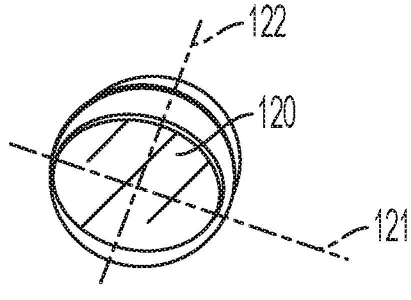

FIG. 15 shows the cross section 120 at and impingement location 125 along the neck 102. Impingement location 125 is generally the location of the neck 102 which impinges against the rim 124 of the cup 106.

The impingement location 125 is preferably chosen to coincide with the position of the rim 124 of the acetabular cup 106 so as to maximise the avoidance thereof and to present the flatter side thereto.

The impingement location 125 may coincide with the aforedescribed posterior angulation transition point 117.

In embodiments, the rotational angle 126 increases (i.e spiraling or rifling) towards the proximal portion 107 of the neck 102. For example, at a distal end of the neck 102, the rotational angle 126 may be 0° and the rotational angle 126 increases towards the distal end of the neck 102.

Preferably, the neck 102 is configured so that the rotational angle 126 increases towards the impingement location 125. In other words, the rotational angle 126 may increase from 0° at the distal end of the neck 102 to 30° at the impingement location 125.

It should be noted that the aforedescribed diminutive postero-superior aspect may be applied to the neck of a conventional implant (i.e. which is symmetric in the longitudinal plane) to increase posterior range of motion until posterior implant impingement.

The foregoing description, for purposes of explanation, used specific nomenclature to provide a thorough understanding of the invention. However, it will be apparent to one skilled in the art that specific details are not required in order to practise the invention. Thus, the foregoing descriptions of specific embodiments of the invention are presented for purposes of illustration and description. They are not intended to be exhaustive or to limit the invention to the precise forms disclosed as obviously many modifications and variations are possible in view of the above teachings. The embodiments were chosen and described in order to best explain the principles of the invention and its practical applications, thereby enabling others skilled in the art to best utilize the invention and various embodiments with various modifications as are suited to the particular use contemplated. It is intended that the following claims and their equivalents define the scope of the invention.

The invention claimed is:

1. A femoral prosthetic component comprising a stem and a neck, the neck defining a centre of rotation when engaging a head articulating within an acetabular cup in use, wherein:

the component has anterior offset so that the centre of rotation is anteriorly offset with respect to a longitudinal axis of the stem; and a proximal portion of the neck has posterior angulation.

2. The component as claimed in claim 1, wherein a proximal portion of the neck forms a trunnion which engages a socket of the head.

3. The component as claimed in claim 1, wherein the anterior offset is defined above a juncture between the neck and the stem.

4. The component as claimed in claim 3, wherein the component is configured so that the juncture generally coincides with an osteotomy plane when implanted in use.

5. The component as claimed in claim 1, wherein the anterior offset is defined by anterior translation between the neck and the stem.

6. The component as claimed in claim 5, wherein the anterior translation is more than 2 mm.

7. The component as claimed in claim 1, wherein the anterior offset is defined by anterior angulation between the neck in the stem.

8. The component as claimed in claim 7, wherein the anterior angulation is defined between a longitudinal axis of a proximal portion of the neck and a frontal plane coincident with a longitudinal axis of the stem.

9. The component as claimed in claim 8, wherein, in an osteotomy plane, the anterior angulation is between 3° and 25°.

10. The component as claimed in claim 8, wherein, in an osteotomy plane, the anterior angulation is approximately 15°.

11. The component as claimed in claim 1, wherein the posterior angulation is defined between a longitudinal axis of the distal portion of the neck and a longitudinal axis of a proximal portion of the neck.

12. The component as claimed in claim 11, in an osteotomy plane, wherein the posterior angulation is between 10° and 30°.

13. The component as claimed in claim 11, in an osteotomy plane, wherein the posterior angulation is approximately 23°.

14. The component as claimed in claim 1, wherein the centre of rotation is anteriorly offset from a frontal plane coincident with the longitudinal axis of the stem by between 3 and 10 mm.

15. The component as claimed in claim 1, wherein the centre of rotation is anteriorly offset from a frontal plane coincident with the longitudinal axis of the stem by approximately 6 mm.

16. The component as claimed in claim 1, wherein an angle defined by a longitudinal axis of a distal end of the neck and a frontal plane defined by the longitudinal axis of the stem is between 5 and 20°.

17. The component as claimed in claim 1, wherein an angle defined by a longitudinal axis of a distal end of the neck and a frontal plane defined by the longitudinal axis of the stem is approximately 8°.

18. The component as claimed in claim 1, wherein the neck defines a posterior angulation transition point between a distal portion and a proximal portion thereof.

19. The component as claimed in claim 18, wherein the transition point generally coincides with a rim of the acetabular cup in use.

20. The component as claimed in claim 18, wherein the transition point is more than halfway along the neck from a distal end of the neck.

21. The component as claimed in claim 18, wherein the transition point is approximately two thirds along the neck from a distal end of the neck.

22. The component as claimed in claim 1, wherein at least one portion along the neck has a cross-section having a diminutive postero-superior aspect.

23. The component as claimed in claim 22, wherein the cross-section defines a major axis and a minor axis and wherein the major axis defines a rotational angle with respect to the longitudinal axis of the stem in the longitudinal plane.

24. The component as claimed in claim 23, wherein the cross-section is elliptical.

25. The component as claimed in claim 23, wherein the rotational angle is more than 10°.

26. The component as claimed in claim 23, wherein the rotational angle is more than 15°.

27. The component as claimed in claim 23, wherein the rotational angle is approximately 30°.

28. The component as claimed in claim 23, wherein the rotational angle increases along the neck from a distal end of the neck.

29. The component as claimed in claim 28, wherein the rotational angle increases to a maximum rotational angle along the neck.

30. The component as claimed in claim 29, wherein the position of the maximum rotational angle is generally coincident with a location of impingement of the neck against a rim of the cup in use.

31. The component as claimed in claim 1, further comprising a further femoral component and wherein the further femoral component is symmetric with the femoral component in a longitudinal plane.

32. Total hip arthroplasty involving the femoral prosthetic component as claimed in claim 1, the arthroplasty comprising implanting the component between a native femur and pelvis so that a centre of rotation defined by the neck when engaging a head articulating within an acetabular cup is anteriorly offset with respect to a longitudinal axis of the stem and a proximal portion of the neck has posterior angulation.

* * * * *